United States Patent [19]

Harris et al.

[11] Patent Number: 5,189,185

[45] Date of Patent: Feb. 23, 1993

[54] PROCESS FOR PREPARING FURAN COMPOSITIONS

[75] Inventors: Eugene Harris, West Chester; Thomas Korte, Cincinnati, both of Ohio

[73] Assignee: Henkel Corporation, Ambler, Pa.

[21] Appl. No.: 485,682

[22] Filed: Feb. 27, 1990

[51] Int. Cl.$^5$ .......................................... C07D 307/30
[52] U.S. Cl. ...................................... 549/486; 512/11
[58] Field of Search ................... 549/214, 486; 512/11

[56] References Cited

PUBLICATIONS

Chemische Berichte 90:2137-2149 (1957); Korte et al.
Angewandte Chemie No. 23, 709-722 (1959) Korte et al.
Bull. Chem. Soc. Jpn., vol. 50, 1977, A. Takeda et al: "A new synthesis of pyrocin and related compounds", pp. 1133-1136.

*Primary Examiner*—Mukund J. Shah
*Assistant Examiner*—Y. N. Gupta

*Attorney, Agent, or Firm*—Ernest G. Szoke; Wayne C. Jaeschke; Daniel S. Ortiz

[57] ABSTRACT

A process for preparing furans of the formula (I)

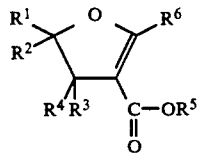

by reacting a furanone of the formula

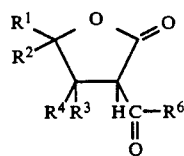

with an organic orthoacid or an orthosilicate in the presence of an acid catalyst at an elevated temperature.

12 Claims, No Drawings

PROCESS FOR PREPARING FURAN COMPOSITIONS

BACKGROUND OF HE INVENTION

1. Field of the Invention

The invention is a process for preparing compositions of the formula

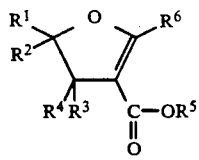
(I)

wherein $R^1$, $R^2$, $R^3$, $R^4$, $R^5$, and $R^6$ are as defined below.

2. Related Art

Compositions of the formula (I) have been made by reacting a monohydric alcohol with a furanone of the formula

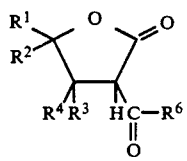

under acidic conditions and an elevated temperature. The yield of the composition (I) is low, due to hydrolysis and the formation of by-products. Processes for preparing these compositions are disclosed in Chemische Berichte 90:2137–2149 (1957) and Angewandte Chemie No. 23, pages 709–752 (Dec. 7, 1959). The processes disclosed in the references provide low yields of the desired furans unless a large excess of the alcohol is utilized. The present invention provides a process by which furans of the formula (I) can be prepared in high yields without use of a large excess of alcohol.

BRIEF DESCRIPTION OF THE INVENTION

According to the present invention a novel process is provided to prepare compositions of the formula (I). According to the present invention, compositions of the formula

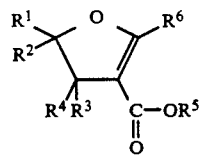

wherein $R^1$, $R^2$, $R^3$, $R^4$, and $R^6$ are each independently hydrogen, alkyl having from 1 to about 20 carbon atoms or alkenyl having from 2 to about 20 carbon atoms the alkyl or alkenyl group can be substituted with halo, alkoxy and aryl, cycloalkyl having from 5 to about 20 carbon atoms which can be substituted with alkyl, alkoxy, alkoxyalkyl, halo, and aryl, aryl having from 6 to about 20 carbon atoms which can be substituted with alkyl, alkoxy, alkoxyalkyl and halo, cycloalkenyl having from about 5 to about 20 carbon atoms which can be substituted with alkyl, alkoxy, alkoxyalkyl and halo, and wherein $R^5$ is aliphatic hydrocarbyl having from 1 to about 8 carbon atoms which can be substituted with halo, alkoxy and aryl, are prepared by a process which comprises:

1) forming a mixture comprising:
   a) a composition of the formula

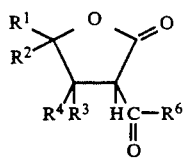

b) at least one of an organic orthoester of the formula $R^7C(OR^5)_3$ an alkyl orthosilicae or alkenyl orthosilicate of the formula

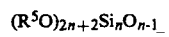
$(R^5O)_{2n+2}Si_nO_{n-1}$ wherein $R^7$ is hydrogen or a hydrocarbyl group having from 1 to about 8 carbon atoms and n is a number of from 1 to about 4.
   c) a catalytic effective amount of an acid and 2) heating the mixture to a temperature effective to react (a) with (b) to form furans of the formula

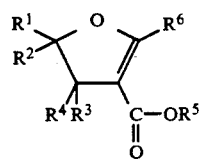

The process is particularly useful in that high yields of the furan (I) can be obtained without the use of a large excess of reagents which must be recovered and recycled to the process.

DETAILED DESCRIPTION OF THE INVENTION

Throughout the specification, composition of formula (I) refers to

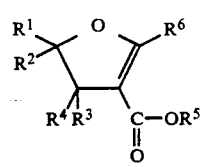
(I)

compositions of formula (II) refers to

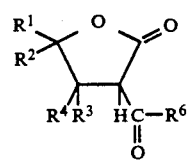
(II)

The furanone starting compounds (II) are well known materials and can be prepared by methods disclosed in Canadian Patent 546,573 and Japanese patent Publication 42-12662.

The organic orthoesters are compounds of the formula $R^7C(OR^5)_3$ wherein $R_7$ is hydrogen or a hydrocarbyl group having from 1 to about 8 carbon atoms such as methylorthoformate, ethyl orthoformate, tripropyl orthoformate, tripentyl orthoformate, trimethyl orthoacetate, triethyl orthoacetate, tripropyl orthoacetate, tributyl orthoacetate, trimethyl orthopropionate, triethyl orthobutyrate, tripropyl orthovalerate, tributyl orthoacetate, tripentyl orthoformate triethyl orthocaprylate and the like.

The orthosilicates are compositions of the formula $(R^5O)_{2n+2}Si_nO_{n-1}$ wherein $R^5$ is as defined above and n is a number of from 1 to about 4. Preferably n is 1.

Generally any organic orthoester or orthosilicate can be used as long as the organic moiety of the alkoxy group of the ester corresponds to the $R^5$ in the furans of the formula (I).

The overall reactions can be written as follows:

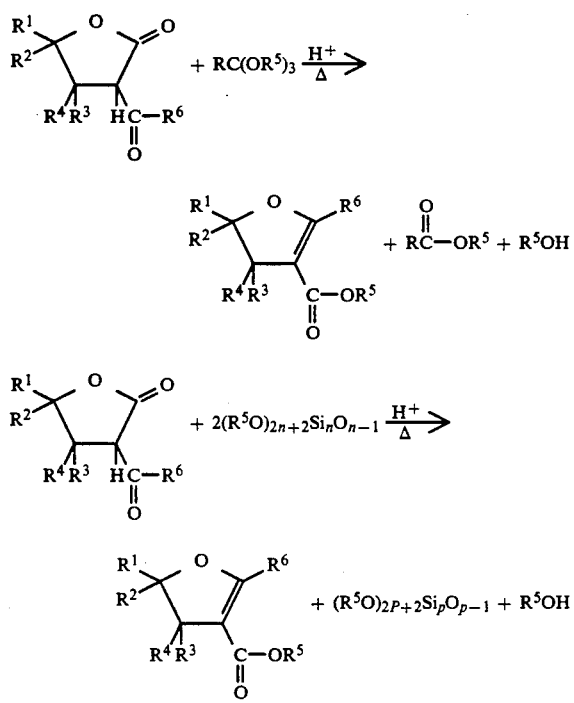

wherein p is equal to 2n.

No water is formed in the process or the water formed is reacted to other species and therefore formation of byproducts due to hydrolysis is substantially reduced.

The alcohol formed in the reaction can be removed from the reaction mixture or can be reacted with a furanone o he formula (II) to produce additional furans of the formula (I).

The furans of the formula (I) product can be recovered from the reaction mixture by known methods such as distillation, extraction capitalization and the like, generally used to recover organic compounds from mixtures.

The reaction is carried out under acid condition. Generally strong organic or inorganic acids can be used. The acids can be present at from about 0.1 to about 10%, preferably from about 0.3 to about 5% and most preferably from about 0.5 to about 4% by weight of the Furanone starting material of the formula (II). Acids such as sulfuric, phosphoric, trifluoroacetic, p-toluene sulfonic, dinonyl naphthalenesulfonic, alkylbenzene sulfonic, alcohol sulfates and the like can be utilized in the process.

The reaction is generally carried out at a temperature from about 50° to about 200° C. Preferably from about 75° C. to about 150° C. Higher temperatures provide for faster reaction rates and shorter reaction times.

If the desired reaction temperature is above the atmospheric boiling point of the reaction mixture, the process can be carried out at an elevated pressure. Autogenous pressure suitable for achieving the required reaction temperature can be used but higher pressures are not harmful.

The mole ratio of furanone of the formula (II) to organic orthoester in the starting reaction mixtures can range from about 1:0.5 to about 1:2. Preferably from about 1:0.85 to about 1:1.5.

The mole ratio of furanone of the formula (II) to orthosilicate can range from about 1:0.25 to about 1:2 preferably from about 1:0.5 to about 1:1.5. In the case of orthosilicate higher mole ratios can be used with lower values of n. The highest mole ratio can be used when n is 1.

Generally the process can be carried out by heating the mixture for a time sufficient to achieve the required amount of reaction. The time for carrying out the process is dependent on the reactants the mole ratios of reactants, the amount of acid catalyst and the temperature to which the reaction mixture is heated. Generally from about one (1) to about 40 hours is sufficient to provide an acceptable yield of the furans product of the formula (I).

The reaction mixture should be maintained substantially water free during the process to obtain the highest yields. The presence of water reduces the yield of the process by formation of by products and reaction with the reagents.

A small amount of dry alcohol of the formula $R^5OH$ wherein $R^5$ is the same as the $R^5$ of the organic orthoester or the orthosilicate can be introduced into the reaction mixture to speed initiation of the reaction but the addition of alcohol to the mixture is not required.

Preferably the compounds prepared by the present process are compounds where $R^1$, $R^2$, $R^3$ and $R^4$ are hydrogen, $R^6$ is alkyl of from 1 to about 6 carbon atoms or alkenyl of from 2 to about 6 carbon atoms and $R^5$ is alkyl of from about 1 to about 5 carbon atoms or alkenyl of from about 2 to about 5 carbon atoms.

The following examples are for illustration only and are not intended to be limiting. In the examples all parts are by weight unless otherwise noted.

EXAMPLE 1

A mixture of 87.9 parts triethyl orthoformate (0.59 moles), 109.3 parts 3-acetyl-5-butyl-dihydro-2(3H)-furanone (0.59 mole), 2.7 parts ethanol (0.059 mole) and 0.87 parts of concentrated sulfuric acid was formed and the mixture heated at reflux (82° C.) for 12 hours. After 12 hours an additional 8.8 parts (0.059 mole) of triethyl orthoformate were added to the reaction mixture and the mixture refluxed for 8 more hours. After 20 hours, gas chromatographic analysis of the reaction mixture indicated that none of the starting furanone was present.

The reaction mixture was neutralized with 0.6 parts sodium hydroxide dissolved in 10 parts of water. The aqueous phase was separated from the organic phase.

The organic phase was stripped on a ROTOVAP under aspirator vacuum to a temperature of 70° C. The residue was distilled at 0.3 torr to yield 112.2 parts of distillate with a purity of 94.8% 2-butyl-4-carbethoxy-5-methyl-2,3-dihydrofuranon. The yield was 86.2% based on 100% reaction of the starting acetyl dihydrofuranone.

EXAMPLE 2

A mixture of 1399 parts of a crude mixture containing 66.8% by weight (5.5 moles) of 3-acetyl-5-propyl-dihydro-2(3H)-furanone, 119 parts triethylorthoformate (8.1 moles) and 21 parts concentrated sulfuric acid were heated at 110° C. and 60 psig (autogenous pressure) for about 7 hours. Gas chromatographic analysis after 6.5 hours indicated that 94% of the starting dihydro-furanone had reacted.

The reaction mixture was neutralized with 17.1 parts of sodium hydroxide flakes and stripped under 15 inches of mercury vacuum with heating to a temperature of 80° C. The stripped mixture was washed with about 10% of the weight of the mixture with water. The water phase was separated, the organic phase was dried under vacuum and filtered. A product in a amount of 1552 parts of crude mixture containing 63.1% by weight of 2-propyl-4-carbethoxy-5-methyl-2,3-dihydrofuran was obtained. This represents a 90.8% yield based on 94% conversion of the starting furanone.

EXAMPLE 3

A mixture of 1498 parts of a crude product containing 71% by weight of 3-acetyl-5-ethyl-dihydro-2(3H)-furanone (6.8 moles) 1190 parts of triethylorthoformate (8.0 moles) and 30 parts concentrated sulfuric acid was heated at 110° C. and 60 psig for about 6.5 hours. After 6 hours, gas chromatographic analysis of the mixture indicated that 94% of the starting dihydrofuranone had reacted. The mixture was neutralized with 24.5 parts of sodium hydroxide flakes. The neutralized mixture was stripped under 15 inches of mercury vacuum while heating to a temperature of 80° C. The mixture was cooled and washed with 10% by weight of the mixture of water. The washed mixture comprised 1632 parts of a crude composition containing 66.9% by weight of 2-ethyl-4-carbethoxy-5-methyl-2,3-dihydrofuran. The yield was 87.0% based on reaction of 94% of the furanone in the starting mixture.

EXAMPLE 4

A mixture of 184 parts of 3-acetyl-5-butyl-dihydro-2(3H)-furanone(1.0 mole), 104 parts tetraethylorthosilicate (0.5 mole), 5 parts dry ethanol (0.1 mole) and .48 parts of concentrated sulfuric acid was heated at 90° C. for 20 hours. After 20 hours analysis of the reaction mixture indicated that 94.5% by weight of the starting furanone had reacted. The reaction mixture was neutralized to a pH of 6 with sodium carbonate, and stripped to remove lower boiling materials. The stripped product was distilled at 10 torr to a temperature of 135° C.

The residue was contacted with 87 parts of toluene to extract remaining product. The toluene was stripped from the extract to provide an additional 23 parts of product. The product was 179 parts containing 93.3% by weight of 2-butyl-4-carbethoxy-5-methyl-2,3-dihydrofuran. The product represents a yield of 81% based on 94.5% of the starting furanone which reacted.

COMPARATIVE EXAMPLE

A reaction mixture containing 83.5 parts of 3-acetyl-5-butyl-dihydro-2(3H)-furanone, 100 parts of anhydrous ethanol and 0.5 parts of concentrated sulfuric acid was refluxed for 6 hours. After 6 hours, the unreacted ethanol was removed under vacuum to a temperature of 69° C. The crude mixture was mixed with 72 parts ether and washed three times with 2N KOH. The organic layer was separated and dried over sodium sulfate and was stripped on a ROTOVAP to recover 77.6 parts of a crude material. The crude material was fractionated to provide 35.3 parts of 2-butyl-4-carbethoxy-5-methyl-2,3-dihydro-2 (3H) furanone. The yield was 37.3 percent based on b 85.2 1 percent reaction of the starting furanone. the mole ratio of ethanol to 3-acetyl-5-butyl-dihydro-2(3H)-furanone was 5:1.

As can be seen from the examples the process of the present invention provides a high yield of the desired product (I) based on the amount of starting furanone (II) reacted when compared to prior art processes.

We claim:

1. A process for preparing compounds of the formula

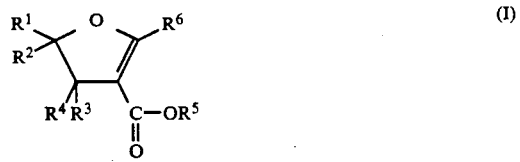

wherein $R^1$, $R^2$, $R^3$, $R^4$ and $R^6$ are each independently hydrogen, alkyl having from 1 to about 20 carbon atoms or alkenyl having from 2 to about 20 carbon atoms the alkyl or alkenyl groups can be substituted with halo, alkoxy and/or aryl, cycloalkyl having from 5 to about 20 carbon atoms which can be substituted with alkyl, alkoxy, alkoxyalky, halo, aryl having from 6 to about 20 carbon atoms which can be substituted with alkyl, alkoxy, alkoxyalky and halo, cycloalkenyl having from about 5 to about 20 carbon atoms which can be substituted with alkyl, alkoxy, alkoxyalkyl and halo, and wherein $R^5$ is aliphatic hydrocarbyl having from 1 to about 8 carbon atoms which can be substituted with halo, alkoxy and aryl which comprises:

(1) forming a mixture comprising
   (a) a composition of the formula

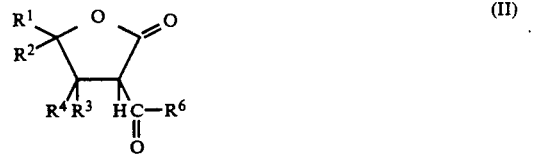

(b) at least one of an organic orthoester of the formula $R^7C (OR^5)_3$ or an orthosilicate of the formula

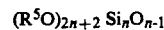

$(R^5O)_{2n+2} Si_nO_{n-1}$ wherein $R^7$ is hydrogen or a hydrocarbyl group having from 1 to about 8 carbon atoms and n is a number of from 1 to about 4;

(c) a catalytic effective amount of an acid; and (2) heating the mixture to a temperature effective to react
   (a) with (b) to form

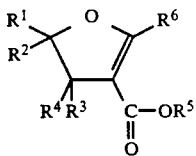

2. A process of claim 1 wherein b) is $R^7C(OR^5)_3$

3. A process of claim 1 wherein b) is $(R^5O)_{2n+n} Si_nO_{n-1}$

4. A process of claim 1 wherein the reaction is carried out at a temperature from about 60° C. to about 200° C.

5. A process of claim 1 wherein a furanone of the formula

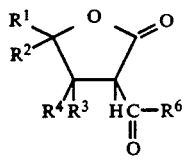

wherein $R^1$, $R^2$, $R^3$ and $R^4$ are hydrogen and $R^6$ is alkyl of from 1 to about 6 carbon atoms is reacted with an organic orthoester of the formula $R^7C(OR^5)_3$ wherein $R^5$ is an alkyl of from 1 to about 4 carbon atoms.

6. A process of claim 1 wherein a furanone of the formula

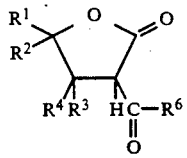

wherein $R^1$, $R^2$, $R^3$, and $R^4$ are hydrogen and $R^6$ is alkyl of from to about 6 carbon atoms is reacted with an orthosilicate of the formula $(R^5O)_{2n+n} Si_nO_{n-1}$ wherein $R^5$ is an alkyl of from 1 to about 4 carbon atoms.

7. A process of claim 5 wherein the reaction is carried out at a temperature of from about 75° C. to about 150° C.

8. A process of claim 7 wherein the catalyst is sulfuric acid.

9. A process of claim 6 wherein the reaction is carried out at a temperature of from about 75° C. to about 150° C.

10. A process of claim 9 wherein the catalyst is sulfuric acid.

11. A process of claim 2 wherein the mole ratio of a) to b) is from about 1.0:0.5 to about 1.0:2.0.

12. A process of claim 3 wherein the mole ratio of a) to b) is from about 1.0:0.25 to about 1.0:2.0.

* * * * *